United States Patent [19]

Drabek et al.

[11] 4,254,136

[45] Mar. 3, 1981

[54] PHENOLIC ESTERS OF N-TRIALKYLUREIDOTHIO-N-METHYL CARBAMIC ACIDS USEFUL AS INSECTICIDES

[75] Inventors: Jozef Drabek, Oberwil, Switzerland; Manfred Böger, Weil am Rhein, Fed. Rep. of Germany

[73] Assignee: Ciba-Geigy Corporation, Ardsley, N.Y.

[21] Appl. No.: 68,261

[22] Filed: Aug. 20, 1979

[30] Foreign Application Priority Data

Aug. 31, 1978 [CH] Switzerland .......................... 9197/78
Mar. 12, 1979 [CH] Switzerland .......................... 2328/79
Jun. 7, 1979 [CH] Switzerland .......................... 5309/79

[51] Int. Cl.³ .................... A01N 43/08; C07D 307/86
[52] U.S. Cl. ..................................... 424/282; 424/285; 424/300; 260/340.9 R; 260/346.73; 260/544 R; 560/115; 560/135; 560/137
[58] Field of Search .......................... 260/346.73, 340.9; 424/285, 282, 300; 560/115, 135, 137

[56] References Cited

U.S. PATENT DOCUMENTS 3,843,688 10/1974 Cleveland .......................... 560/135
4,169,894 10/1979 D'Silva .............................. 260/340.9

*Primary Examiner*—Henry R. Jiles
*Assistant Examiner*—Bernard Dentz
*Attorney, Agent, or Firm*—Frederick H. Rabin

[57] ABSTRACT

Compounds of the formula I

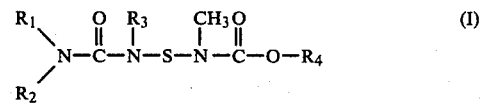

wherein $R_1$ and $R_2$ are each $C_1$–$C_4$-alkyl, $R_3$ is $C_1$–$C_{10}$-alkyl or $C_3$–$C_6$-cycloalkyl and $R_4$ is 2-isopropoxyphenyl; 2-(1,3-dioxolan-2-yl)-phenyl; 2-methylthiomethylphenyl; 2-ethylthiomethylphenyl; 2-isopropylphenyl; 3,5-dimethyl-4-methylthiophenyl or 2,2-dimethyl-(2H,3H)-dihydrobenzofuran-7-yl having valuable pesticidal in particular insecticidal properties.

12 Claims, No Drawings

PHENOLIC ESTERS OF N-TRIALKYLUREIDOTHIO-N-METHYL CARBAMIC ACIDS USEFUL AS INSECTICIDES

The present invention relates to novel (N-methyl-carbamoylphenoxy)-(N',N'',N''-trialkyl-urea)-N,N'-sulfide derivatives which have an action against pests, especially against insect pests, to processes for producing these derivatives, to insecticidal compositions containing them as active ingredients, and to processes for the control of insect pests by application of the novel compounds.

From the G.B. Pat. No. 1,506,089 are already known, inter alia, compounds of the formula

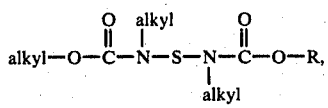

wherein R is a substituted phenyl group, as insecticides.

According to the present invention, there are provided novel compounds of this type which likewise have an action against pests, especially against insect pests, and which, by virtue of their advantageous biological properties, are particularly suitable for practical application.

The novel (N-methylcarbamoyl-phenoxy)-(N',N'',N''-trialkyl-urea)-N,N'-sulfide derivatives according to the invention correspond to the formula I

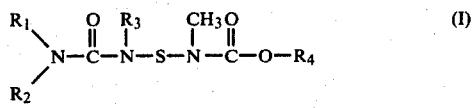

wherein $R_1$ and $R_2$ are each a $C_1$–$C_4$-alkyl group, $R_3$ is a $C_1$–$C_{10}$-alkyl group or $C_3$–$C_6$-cycloalkyl group, and $R_4$ is a 2-isopropoxyphenyl, 2-(1,3-dioxolan-2-yl)-phenyl, 2-methylthiomethylphenyl, 2-ethylthiomethylphenyl, 2-isopropylphenyl, 3,5-dimethyl-4-methylthiophenyl or 2,2-dimethyl-(2H,3H)-dihydrobenzofuran-7-yl group.

Alkyl groups as $R_1$ and $R_2$, which are identical or different, and also as $R_3$ can be branched-chain or straight-chain. Suitable substituents of this type are for example: the methyl, ethyl, n- and i-propyl, n-, i-, s- and t-butyl groups, and also the n-pentyl, n-hexyl, n-octyl and n-decyl group.

Preferred types of substituents and combinations of these among each other in the compounds of the formula I are as follows:

(1) for $R_1$ and $R_2$: methyl or ethyl;
(2) for $R_3$: $C_1$–$C_8$-alkyl (particularly $C_1$–$C_4$-alkyl and in particular methyl) and cyclopropyl; and
(3) for $R_4$: 2,2-dimethyl-(2H,3H)-dihydrobenzofuran-7-yl.

In accordance with the present invention it has now surprisingly been found that the said compounds of the formula I have an excellent insecticidal action with a broad spectrum. They can be used for example for controlling insects of the orders: Lepidoptera, Colleoptera, Heteroptera, Diptera, Orthoptera and Homoptera. In this connection, it is to be emphasised that the compounds of the formula I are characterised by a particularly strongly marked activity against insects of the last-mentioned order (Homoptera), and especially against insects of the family Aphididae. It has in this respect been established that the compounds according to the invention have both a contact and a systemic action against a considerable number of representatives of the stated family (for example *Aphis fabae, Aphis craccivora* and *Myzus persicae*) which can be controlled by other means only with great difficulty.

By virtue of the properties mentioned above, the compounds of the formula I are particularly suitable according to the invention for the control of insects, especially insects which damage plants, in crops of useful plants and ornamental plants, principally in the field of vegetable and fruit cultivation, including citrus fruits.

Furthermore, the compounds of the formula I have a valuable action against phytoparasitic nematodes and also against acarids, particularly ectoparasitic acarids (mites and ticks), for example of the families Ixodidae, Argasidae and Dermanyssidae.

It has also been verified according to the invention that the pesticidal properties described in the foregoing are coupled with a toxicity to warm-blooded animals which is advantageous for practical application in the field of plant protection.

The compounds of the formula I are produced by processes analogous to known processes, for example by reacting (a) a compound of the formula II

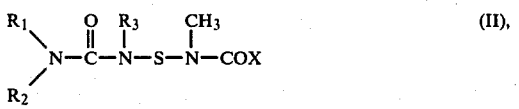

in the presence of a base, with a compound of the formula III

or (b) a compound of the formula IV

in the presence of a base, with a compound of the formula V

the symbols $R_1$ to $R_4$ in the formulae II, III, IV and V having the meanings already given for formula I, X' being a halogen atom, particularly a fluorine atom, and X'' being a halogen atom, especially a chlorine atom.

The processes (a) and (b) are performed at a reaction temperature of between −50° C. and +130° C., preferably at between −10° C. and +100° C., under normal or slightly elevated pressure and in the presence of a solvent or diluent which is inert to the reactants.

Bases suitable for these processes are in particular: tertiary amines, such as trialkylamines, pyridines and dialkylanilines, also hydroxides, oxides, carbonates and bicarbonates of alkali metals and alkaline-earth metals, as well as alkali metal alcoholates, for example potassium tert-butylate and sodium methylate.

Suitable solvents or diluents are for example: ethers and ethereal compounds, such as diethyl ether, di-isopropyl ether, dioxane, tetrahydrofuran; aliphatic and aromatic hydrocarbons, especially benzene, toluene, xylenes; and ketones, such as acetone, methyl ethyl ketone and cyclohexanone.

The starting materials of the formulae III, IV and V used in the processes described in the foregoing are known, and they can be produced by methods analogous to known methods (see for example G.B. Pat. No. 1,138,347; U.S. Pat. Nos. 3,474,171 and 3,111,539 and German Offenlegungsschrift No. 1,910,588).

The starting materials of the formula II are however novel and likewise form part of the subject matter of the invention. They are obtained from known precursors by reacting for example a compound of the formula VI

(VI), in the presence of a base, with a compound of the formula VII

CH$_3$—NH—COX'               (VII), the symbols $R_1$, $R_2$, $R_3$ and $X'$ in the formulae VI and VII having the meanings already mentioned, and "Hal" being a halogen atom.

The process for producing the starting materials of the formula II is performed preferably in the presence of a solvent or diluent inert to the reactants, at a reaction temperature of $-50°$ C. to $+130°$ C. and under normal pressure. Suitable bases and solvents for this process are the substances already mentioned for the processes (a) and (b) described in the foregoing.

The compounds of the formula I are used according to the invention on their own, or they form a constituent of compositions which also contain suitable carriers or additives or mixtures of such substances. Suitable carriers and additives can be solid or liquid and they correspond to the substances common in formulation practice, such as natural or regenerated substances, solvents, dispersing agents, wetting agents, adhesives, thickeners, binders and/or fertilisers.

The insecticidal action of the compositions according to the invention can be substantially broadened by the addition of other acaricides and/or insecticides. Suitable additives are for example: organic phosphorus compounds; nitrophenols and derivatives thereof; formamidines; ureas; pyrethrin-like compounds; carbamates and chlorinated hydrocarbons.

The compositions according to the invention can be in the form of dusts, granulates, dispersions, solutions and suspensions, as well as in the form of water-dispersible wettable powders, pastes, emulsions and emulsion concentrates, and can be applied in these forms.

The content of active substance (compound of the formula I) in the compositions described above is between 0.1 and 95%; it is to be mentioned in this connection that with application from an aeroplane, or by means of other suitable application devices, also higher concentrations can be used.

The compounds of the formula I can be formulated for example as follows:

Emulsion concentrate I 20 parts by weight of the active substance are dissolved in 70 parts by weight of xylene, and to the solution are added 10 parts by weight of an emulsifying agent consisting of a mixture of an arylphenylpolyglycol ether and the calcium salt of dodecylbenzenesulfonic acid.

Water can be added in any proportion to the emulsion concentrate to form a milky emulsion.

Emulsion concentrate II 5 to a maximum of 30 parts by weight of active substance are dissolved at room temperature, with stirring, in 30 parts by weight of dibutylphthalate, 10 parts by weight of Solvent 200 (low-viscous, highly aromatic petroleum distillate), 15 to 35 parts by weight of Dutrex 238 FC (viscous highly aromatic petroleum distillate), and to the solution are added 10 parts by weight of an emulsifier mixture consisting of castor-oil polyglycol ether and the calcium salt of dodecylbenzenesulfonic acid.

The emulsion concentrate thus obtained produces milky emulsions when water is added.

Wettable powder 5 to 30 parts by weight of the active substance are thoroughly mixed, in a mixing apparatus, with 5 parts by weight of an absorbing carrier material (Kieselsäure K 320 [silicic acid] or Wessalon S) and 55 to 80 parts by weight of a carrier material (bolus alba or Kaolin B 24) and a dispersing agent mixture consisting of 5 parts by weight of a sodium lauryl sulfonate and 5 parts by weight of an alkyl-aryl-polyglycol ether.

This mixture is ground to 5–15 μm in a dowelled disc mill or air jet mill. A good suspension is obtained by adding water to the wettable powder thus produced.

Dust 5 parts by weight of finely ground active substance are thoroughly mixed with 2 parts by weight of a precipitated silicic acid and 93 parts by weight of talc.

| Pour-on solution | |
|---|---|
| active substance | 30.0 g |
| sodium dioctylsulfosuccinate | 3.0 g |
| benzyl alcohol | 48.0 g |
| peanut oil | 19.8 g |
| | 100.8 g = 100 ml |

The active substance is dissolved in the benzyl alcohol with stirring and if necessary with slight heating. The sodium dioctylsulfosuccinate and peanut oil are added to the solution, and are dissolved with heating and thorough stirring.

The Examples which follow serve to further illustrate the invention.

EXAMPLE 1

(a) Production of (N-methylcarbamoylfluoride)-N',N'',N'''-trimethyl-urea)-N,N'-sulfide (starting material)

14.85 ml of methylisocyanate was added at a temperature of −50° C., with stirring, to a solution of 5 g of anhydrous hydrofluoric acid in 5 ml of toluene, and the reaction mixture was subsequently stirred for 2 hours. To the solution obtained in this manner was added 42.1 g of N,N,N'-trimethylurea sulfenyl chloride, and at a temperature of −50° to −20° C. there was added dropwise, with stirring, 34.55 ml of triethylamine. The reaction mixture was afterwards stirred for 2 hours at −20° C. and then for 10 hours at room temperature. After filtration under suction, the filtrate was concentrated in a rotary evaporator. The crude product was distilled off under high vacuum to obtain (N-methylcarbamoyl-fluoride)-(N',N'',N''-trimethyl-urea)-N,N'-sulfide of the formula

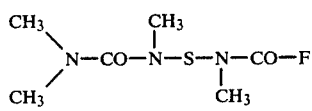

as an orange-coloured liquid having a b.p. of 78°–83° C. at 0.04 mb.

The following starting materials of the formula IIa

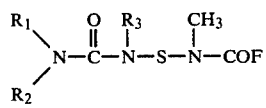

are obtainable in an analogous manner.

| $R_1$ | $R_2$ | $R_3$ | Physical data |
|---|---|---|---|
| $CH_3$ | $CH_3$ | ▷− | b.p.: 100–105° C./0,09 mb |
| $CH_3$ | $CH_3$ | n-$C_4H_9$ | b.p.: 105–110° C./0,08 mb |
| $CH_3$ | $CH_3$ | n-$C_6H_{13}$ | b.p.: 125–127° C./0,09 mb |
| $CH_3$ | $CH_3$ | n-$C_8H_{17}$ | b.p.: 140–145° C./0,13 mb |
| $CH_3$ | $CH_3$ | n-$C_{10}H_{21}$ | |
| $C_2H_5$ | $C_2H_5$ | $CH_3$ | b.p.: 97–99° C./0,11 mb |
| $C_2H_5$ | $C_2H_5$ | n-$C_4H_9$ | b.p.: 120–121° C./0,08 mb |
| n$C_3H_7$ | n$C_3H_7$ | $CH_3$ | b.p.: 109–111° C./0,07 mb |
| i$C_3H_7$ | i$C_3H_7$ | $CH_3$ | b.p.: 96–103° C./0,11–0,2 mb |
| n$C_4H_9$ | $CH_3$ | n-$C_4H_9$ | b.p.: 125–128° C./0,07 mb |
| n-$C_4H_9$ | n-$C_4H_9$ | $CH_3$ | b.p.: 119–124°/0,08 mb |
| n-$C_4H_9$ | n-$C_4H_9$ | n-$C_4H_9$ | b.p.: 135–136°/0,08 mb |
| $CH_3$ | $CH_3$ | ⟨H⟩− | |

(b) Production of (N-methylcarbamoyloxy-(2,2-dimethyl-(2H,3H)-dihydrobenzofuran-7-yl))-(N',N'',N'''-trimethyl-urea)-N,N'-sulfide (final product)

To a solution of 8.75 g of 2,2-dimethyl-(2H,3H)-dihydro-7-hydroxy-benzofuran in 80 ml of toluene was added, with stirring, 7.4 ml of triethylamine, and subsequently there was added dropwise, at a maximum of 30° C., 11.15 g (N-methylcarbamoylfluoride)-(N',N'',N'''-trimethyl-urea)-N,N'-sulfide. The reaction mixture was subsequently stirred for 16 hours at room temperature and for 2 ½ hours at 45° C.; it was then filtered and concentrated by evaporation. The crude product was taken up in benzene and washed 4 times with 50 ml of water each time; the organic phase was dried over sodium sulfate and then concentrated by evaporation to thus yield (N-methylcarbamoyloxy-(2,2-dimethyl-(2H,3H)-dihydrobenzofuran-7-yl)-N',N'',N'''-trimethyl-urea)-N,N'-sulfide of the formula

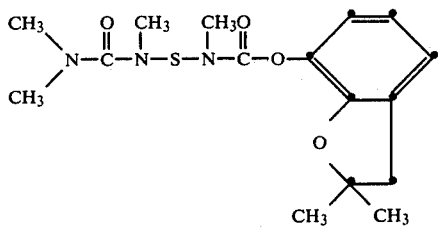

(Compound No. 1) in the form of yellow oil having a refractive index of $n_D^{45}$: 1.5308.

The following compounds of the formulae IA, IB and IC can be produced by a process analogous to the production process described in the foregoing:

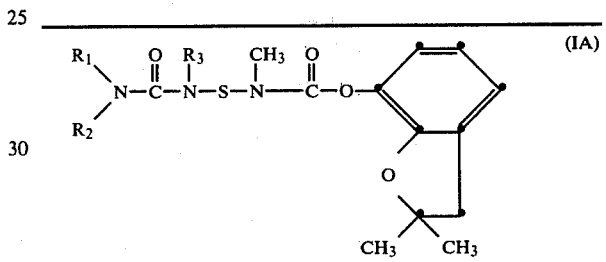

| Comp. No. | $R_1$ | $R_2$ | $R_3$ | Physical data |
|---|---|---|---|---|
| 2 | $CH_3$ | $CH_3$ | ▷− | $n_D^{45}$: 1,5329 |
| 3 | $CH_3$ | $CH_3$ | n-$C_4H_9$ | |
| 4 | $CH_3$ | $CH_3$ | n-$C_6H_{13}$ | $n_D^{30}$: 1,5119 |
| 5 | $CH_3$ | $CH_3$ | n-$C_8H_{17}$ | $n_D^{30}$: 1,5060 |
| 6 | $CH_3$ | $CH_3$ | n-$C_{10}H_{21}$ | |
| 7 | $C_2H_5$ | $C_2H_5$ | $CH_3$ | $n_D^{40}$: 1,5239 |
| 8 | $C_2H_5$ | $C_2H_5$ | n-$C_4H_9$ | $n_D^{40}$: 1,5109 |
| 9 | n-$C_3H_7$ | n-$C_3H_7$ | $CH_3$ | $n_D^{40}$: 1,5160 |
| 10 | i-$C_3H_7$ | i-$C_3H_7$ | $CH_3$ | $n_D^{40}$: 1,5170 |
| 11 | n-$C_4H_9$ | $CH_3$ | n-$C_4H_9$ | $n_D^{40}$: 1,5040 |
| 12 | n-$C_4H_9$ | n-$C_4H_9$ | $CH_3$ | $n_D^{40}$: 1,5053 |
| 13 | n-$C_4H_9$ | n-$C_4H_9$ | n-$C_4H_9$ | $n_D^{40}$: 1,4971 |
| 14 | $CH_3$ | $CH_3$ | ⟨H⟩− | |

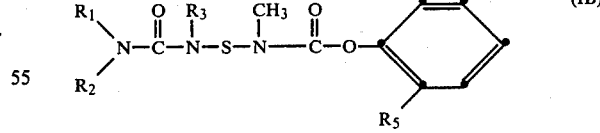

| Comp. No. | $R_1$ | $R_2$ | $R_3$ | $R_5$ | Physical data |
|---|---|---|---|---|---|
| 15 | $CH_3$ | $CH_3$ | $CH_3$ | i-$C_3H_7O-$ | $n_D^{40}$: 1,5178 |
| 16 | $CH_3$ | $CH_3$ | $CH_3$ |  | $n_D^{20}$: 1,5349 |
| 17 | $CH_3$ | $CH_3$ | $CH_3$ | $CH_3SCH_2-$ | |
| 18 | $CH_3$ | $CH_3$ | $CH_3$ | $C_2H_5SCH_2-$ | |
| 19 | $CH_3$ | $CH_3$ | $CH_3$ | i-$C_3H_7$ | $n_D^{30}$: 1,5260 |
| 20 | $CH_3$ | $CH_3$ | n-$C_8H_{17}$ | i-$C_3H_7$ | $n_D^{20}$: 1,4903 |

-continued

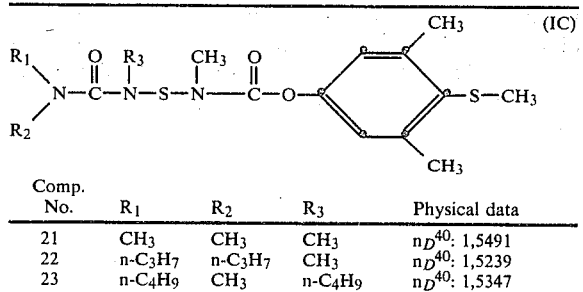

| Comp. No. | R₁ | R₂ | R₃ | Physical data |
|---|---|---|---|---|
| 21 | CH₃ | CH₃ | CH₃ | $n_D^{40}$: 1,5491 |
| 22 | n-C₃H₇ | n-C₃H₇ | CH₃ | $n_D^{40}$: 1,5239 |
| 23 | n-C₄H₉ | CH₃ | n-C₄H₉ | $n_D^{40}$: 1,5347 |

EXAMPLE 2

Insecticidal stomach poison action: *Spodoptera littoralis, Dysdercus fasciatus* and *Heliothis virescens*

Cotton plants were sprayed with an aqueous emulsion containing 0.05% of the compound to be tested (obtained from a 10% emulsifiable concentrate). After drying of the coating, larvae of the species *Spodoptera littoralis* (L3 stage), *Dysdercus fasciatus* (L4) and *Heliothis virescens* (L3), respectively, were settled on the plants. Two plants were used for each test compound and for each test species, and an assessment of the destruction of larvae was made 2, 4, 24 and 48 hours after commencement of the test. The tests were carried out at 24° C. with 60% relative humidity.

Compounds of the formula I according to Example 1 exhibited in the above test a good action against larvae of the species *Spodoptera littoralis, Dystercus fasciatus* and *Heliothis virescens.*

EXAMPLE 3

Insecticidal stomach poison action: *Leptinotarsa decemlineata*

The test described in Example 2 was repeated using larvae of the species *Leptinotarsa decemlineata* (L3) and using potato plants in place of cotton plants, the procedure otherwise remaining the same.

Compounds of the formula I exhibited in this test a good action against larvae of the species *Leptinotarsa decemlineata.*

EXAMPLE 4

Insecticidal contact action: *Myzus persicae*

Plants (*Vicia fabae*) grown in water were each infested, before the commencement of the test, with about 200 individuals of the species *Myzus persicae.* Three days later, the plants treated in this manner were sprayed from a distance of 30 cm until dripping wet with a solution containing 10 and 1 ppm, respectively, of the compound to be tested. Two plants were used for each test compound and for each concentration, and an evaluation of the attained degree of destruction of the insects was made after a further 24 hours.

Compounds of the formula I according to Example 1 exhibited in the above test a good action against insects of the species *Myzus persicae.*

EXAMPLE 5

Insecticidal systemic action: *Aphis craccivora*

Rooted bean plants were transplanted into pots containing 600 ccm of soil, and subsequently 50 ml of a solution of the compound to be tested (obtained from a 25% wettable powder) at a concentration of 25 ppm, 5 ppm and 1 ppm, respectively, was poured directly onto the soil. After 24 hours, lice of the species *Aphis craccivora* were settled onto the parts of the plants above the soil, and a plastics cylinder was placed over each plant in order to protect the lice from a possible contact or gas effect of the test substance. The evaluation of the achieved destruction of lice was made after 24 and 48 hours, respectively, after commencement of the test. Two plants, each in a separate pot, were used for each concentration dose of test substance. The test was carried out at 25° C. with 70% relative humidity.

The compounds according to Example 1 exhibited in the above test a good systemic action against insects of the species *Aphis craccivora.*

What is claimed is:

1. A compound of the formula I

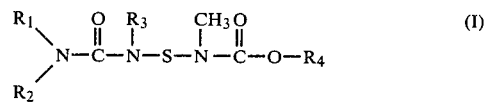

wherein R₁ and R₂ each independently of the other is C₁–C₄-alkyl, R₃ is C₁–C₁₀-alkyl or C₃–C₆-cycloalkyl, and R₄ is 2-isopropoxyphenyl; 2-(1,3-dioxolan-2-yl)-phenyl; 2-methylthiomethylphenyl; 2-ethylthiomethylphenyl; 2-isopropylphenyl; 3,5-dimethyl-4-methylthiophenyl; or 2,2-dimethyl-(2H,3H)-dihydrobenzofuran-7-yl.

2. A compound of the formula I

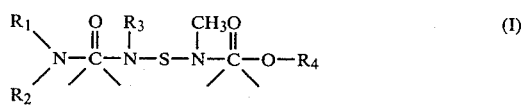

wherein R₁ and R₂ each independently of the other is C₁–C₄-alkyl, R₃ is C₁–C₁₀-alkyl or C₃–C₆-cycloalkyl, and R₄ is 2-(1,3-dioxolan-2-yl)-phenyl; or 2,2-dimethyl-(2H,3H)-dihydrobenzofuran-7-yl.

3. A compound as claimed in claim 2 wherein R₁ and R₂ each independently of the other is methyl or ethyl.

4. A compound as claimed in claim 2 wherein R₃ is C₁–C₄-alkyl or cyclopropyl.

5. A compound as claimed in claim 4 wherein R₃ is methyl or cyclopropyl.

6. A compound as claimed in any one of claims 2 to 4 wherein R₄ is 2,2-dimethyl-(2H,3H)-dihydrobenzofuran-7-yl.

7. A compound as claimed in claim 2 of the formula

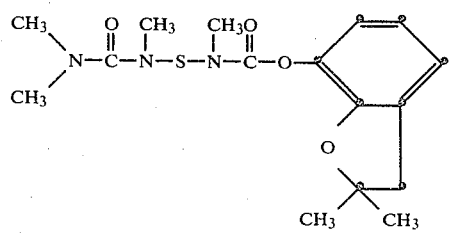

8. A compound as claimed in claim 2 of the formula

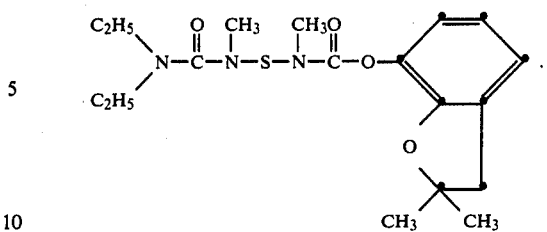

10. A compound as claimed in claim 2 of the formula

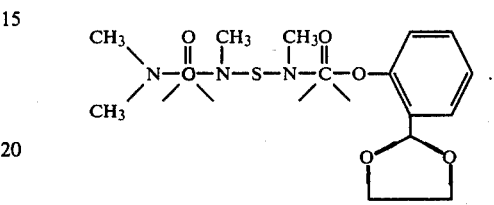

9. A compound as claimed in claim 2 of the formula

11. An insecticidal composition comprising an insecticidally effective amount of a compound as claimed in claim 2 together with an inert, solid or liquid diluent or carrier therefor.

12. A method of controlling insect pests at a locus which method comprises applying to said locus an insecticidally effective amount of a compound as claimed in claim 2.

* * * * *

UNITED STATES PATENT AND TRADEMARK OFFICE
CERTIFICATE OF CORRECTION

PATENT NO. : 4,254,136
DATED : MARCH 3, 1981
INVENTOR(S) : JOZEF DRABEK AND MANFRED BOGER

It is certified that error appears in the above-identified patent and that said Letters Patent are hereby corrected as shown below:

Claim 2, column 8, line 35 reads:

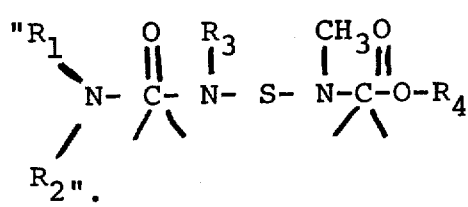

Should read:

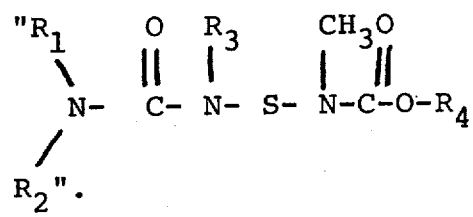

UNITED STATES PATENT AND TRADEMARK OFFICE
CERTIFICATE OF CORRECTION

PATENT NO. : 4,254,136
DATED : MARCH 3, 1981
INVENTOR(S) : JOZEF DRABEK AND MANFRED BOGER

It is certified that error appears in the above-identified patent and that said Letters Patent are hereby corrected as shown below:

Claim 10, column 10, line 15 reads:

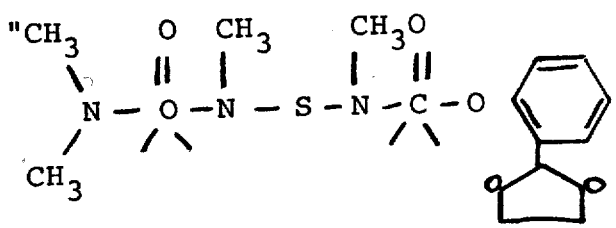

Should read:

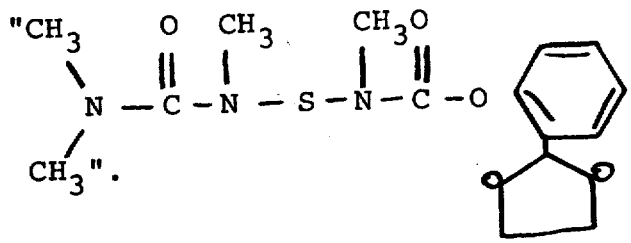

Signed and Sealed this

Twelfth Day of May 1981

[SEAL]

Attest:

RENE D. TEGTMEYER

Attesting Officer     Acting Commissioner of Patents and Trademarks